US007635342B2

(12) United States Patent
Ferry et al.

(10) Patent No.: US 7,635,342 B2
(45) Date of Patent: Dec. 22, 2009

(54) SYSTEM AND METHODS FOR MEDICAL DEVICE ADVANCEMENT AND ROTATION

(75) Inventors: Steven J. Ferry, Excelsior, MN (US); Jennifer R. Finney, St. Louis, MO (US); Cam Habeger, Big Lake, MN (US); Vincent Hackenmueller, Monticello, MN (US); Andrew F. Hall, St. Charles, MO (US); Reed A. Houge, Buffalo, MN (US); Scott G. Klimek, Spring Lake Park, MN (US); Michael J. Pikus, Golden Valley, MN (US)

(73) Assignee: Stereotaxis, Inc., St. Louis, MO (US)

( * ) Notice: Subject to any disclaimer, the term of this patent is extended or adjusted under 35 U.S.C. 154(b) by 932 days.

(21) Appl. No.: 10/858,485

(22) Filed: Jun. 1, 2004

(65) Prior Publication Data
US 2006/0041245 A1  Feb. 23, 2006

Related U.S. Application Data

(63) Continuation-in-part of application No. 10/138,710, filed on May 3, 2002, now Pat. No. 7,276,044.

(60) Provisional application No. 60/288,879, filed on May 6, 2001.

(51) Int. Cl.
| A61B 5/00 | (2006.01) |
| A61M 25/00 | (2006.01) |
| A61M 31/00 | (2006.01) |
| A61F 11/00 | (2006.01) |

(52) U.S. Cl. .......... 600/585; 604/510; 606/108
(58) Field of Classification Search ............ 600/585; 604/510; 606/108
See application file for complete search history.

(56) References Cited

U.S. PATENT DOCUMENTS

| 2,948,513 | A | * | 8/1960 | Krohn-Holm | ............... 254/396 |
| 3,784,046 | A | * | 1/1974 | Cata | ............... 220/826 |
| 5,253,845 | A | * | 10/1993 | Wilbert | ............... 254/30 |
| 5,288,556 | A | * | 2/1994 | Lemelson | ............... 428/408 |
| 5,318,442 | A | * | 6/1994 | Jeffcoat et al. | ............... 433/72 |
| 5,361,768 | A | | 11/1994 | Webler et al. | |
| 5,380,338 | A | * | 1/1995 | Christian | ............... 606/130 |
| 5,779,623 | A | * | 7/1998 | Bonnell | ............... 600/114 |
| 5,827,313 | A | | 10/1998 | Ream | |
| 5,957,941 | A | | 9/1999 | Ream | |
| 6,077,219 | A | * | 6/2000 | Viebach et al. | ............... 600/114 |
| 6,319,227 | B1 | | 11/2001 | Munsouri-Ruiz | |

* cited by examiner

*Primary Examiner*—Max Hindenburg
*Assistant Examiner*—Sean P Dougherty
(74) *Attorney, Agent, or Firm*—Harness, Dickey & Pierce, P.L.C.

(57) ABSTRACT

A system for moving an elongate medical device has at least one drive element for engaging and moving an elongate medical device. Various embodiments provide for moving the separate inner and outer elements of a telescoping medical device. Some systems also provide for the rotation of a rotatable distal element on a rotatable medical device or the rotation of extension element in a telescoping medical device.

16 Claims, 14 Drawing Sheets

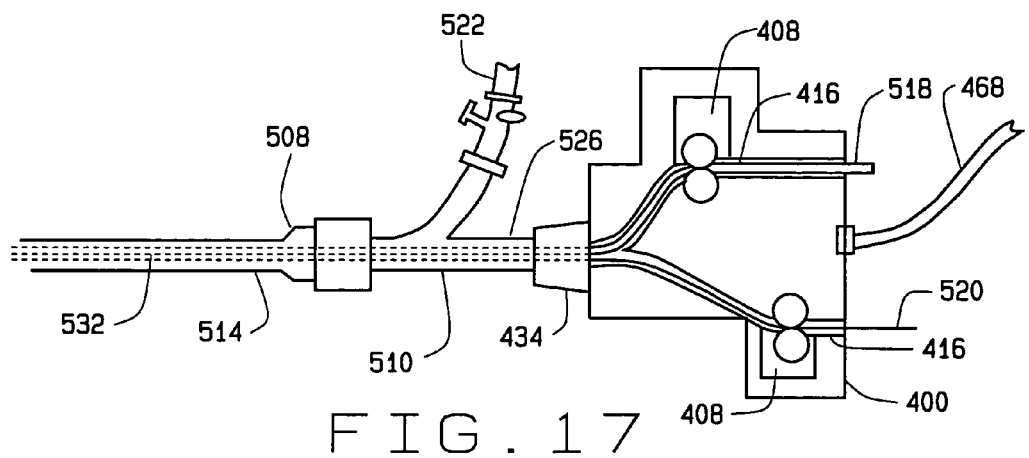
FIG. 17
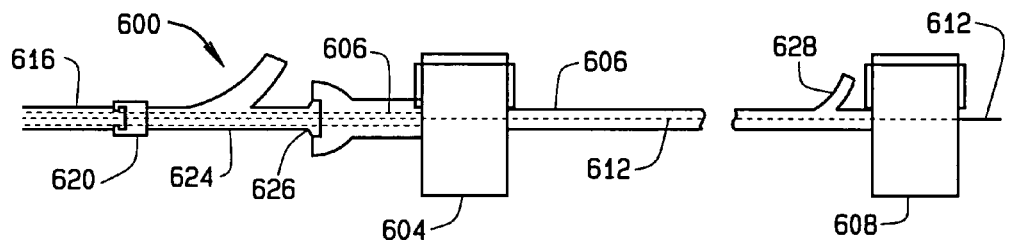
FIG. 18
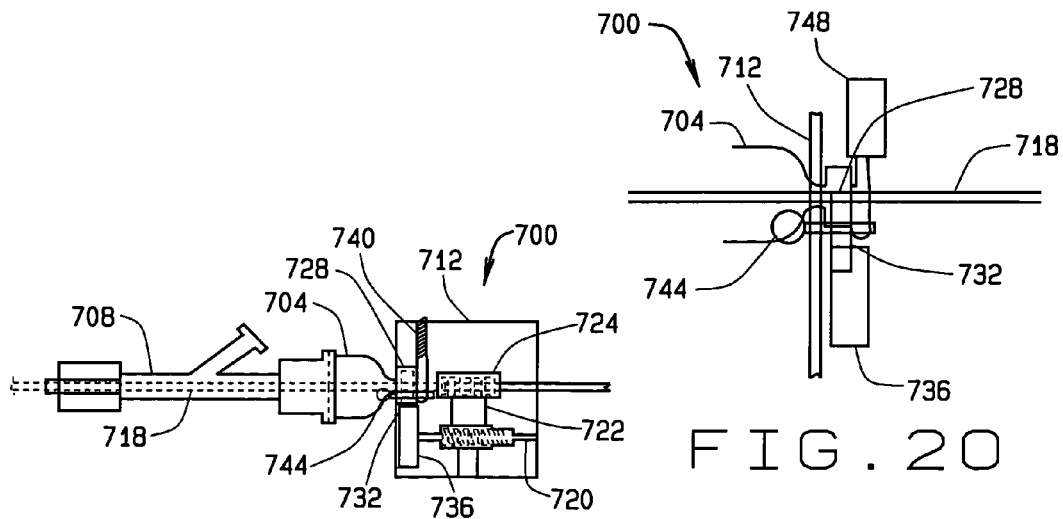
FIG. 19
FIG. 20

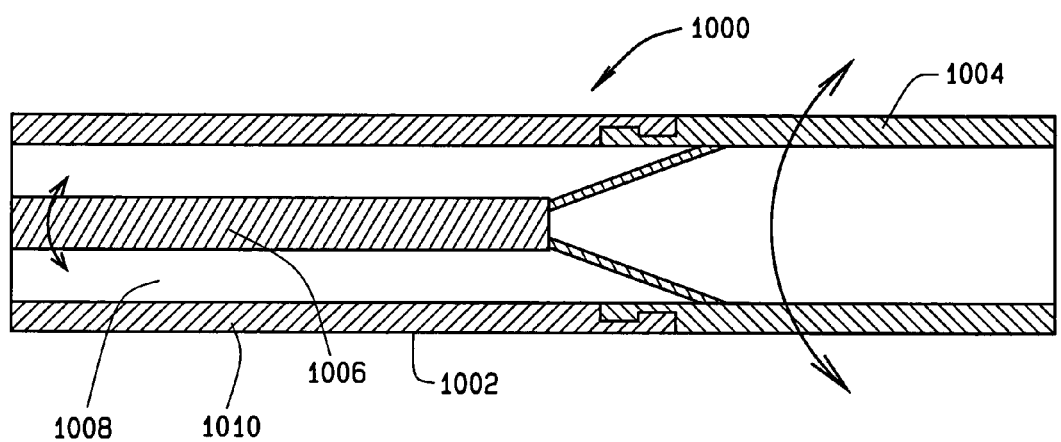
FIG. 25
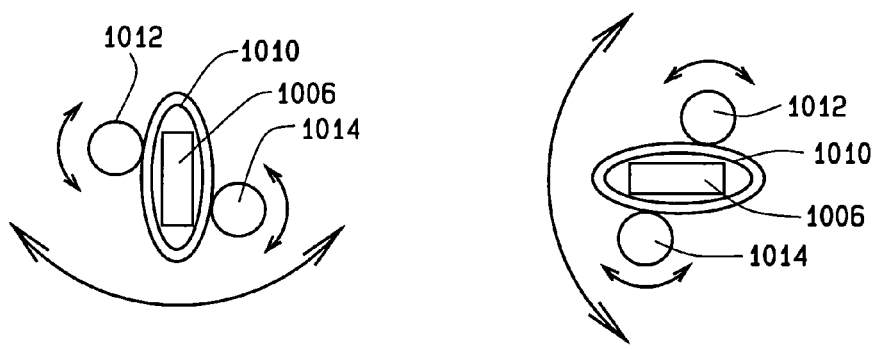
FIG. 26A
FIG. 26B

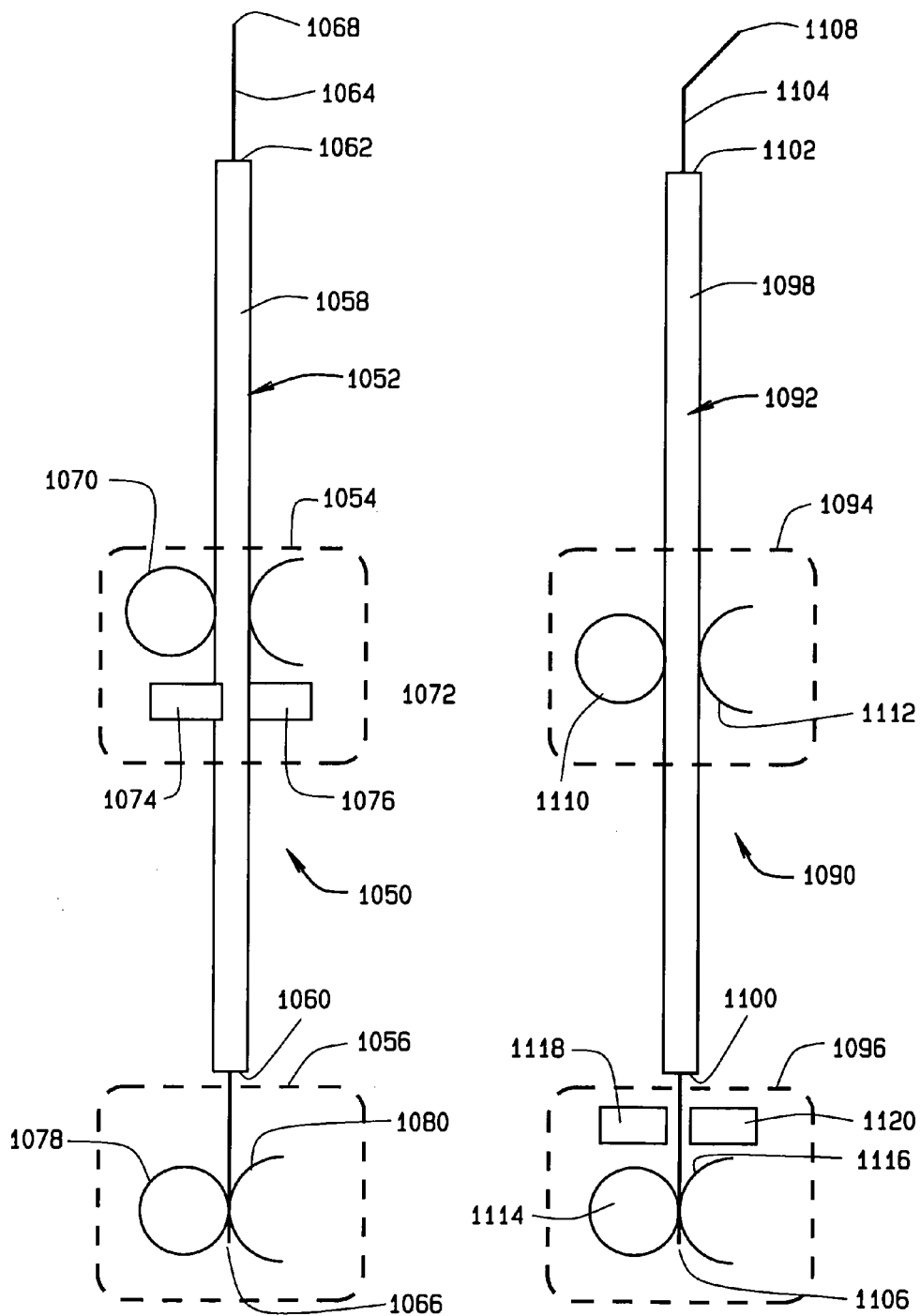

SYSTEM AND METHODS FOR MEDICAL DEVICE ADVANCEMENT AND ROTATION

CROSS-REFERENCE TO RELATED APPLICATIONS

This application is a continuation-in-part of U.S. patent application Ser. No. 10/138,710 filed on May 3, 2002, which claims priority to U.S. Provisional Patent Application No. 60/288,879, filed May 6, 2001. The disclosures of the above applications are incorporated herein by reference in their entirety.

BACKGROUND OF THE INVENTION

A variety of techniques are currently available to physicians for controlling elongate medical devices such as catheters, endoscopes and other surgical tools within a patient. For example, magnetic steering techniques provide computer-assisted control of a catheter tip while allowing an operating physician to remain outside the operating room x-ray field. Thus the physician, freed from having to manually steer the catheter tip.

However, the physician still must manually advance the device once the distal end of the device is the desired orientation. A number of medical procedures call for more than one elongate medical device to be navigated and positioned within a patient's body. For example, during a percutaneous transluminal coronary angioplasty (PTCA), an "over-the-wire" (OTW) procedure may be performed. A guide wire is placed into a lumen of an OTW catheter. The two devices are inserted together and advanced to the procedure site by successively advancing the guidewire and then the catheter over the guidewire.

In another procedure known as rapid wire exchange (RWE), a guide wire is inserted and navigated to the procedure site. A RWE catheter (also known as a "monorail" catheter) is placed over the proximal end of the guide wire and is advanced over the wire into the patient. The RWE catheter has a short guide wire lumen that is open at both ends, thus facilitating rapid exchange of the catheter with another catheter during the procedure.

It is desirable, of course, to minimize physician fatigue and x-ray exposure during a surgical procedure. Advancing one elongate medical device within and/or next to another elongate device, however, is frequently made difficult by a number of factors, including but not limited to the lengths and frictional characteristics of the devices.

SUMMARY OF THE INVENTION

In many interventional medical procedures multiple devices are inserted into a patient's anatomy for diagnosis and therapy. The present invention is directed to a motion control mechanism for moving at least one elongate medical device and addresses the need for computer control of the motion of multiple devices, either independently or in tandem, when such procedures are performed by robotic or other remotely actuated means. The motion control mechanism can perform the functions of device advancement and retraction, or axial rotation of at least one of the devices, or any combination of these motions. A computer can control these motions in such a manner as to be able to produce a discrete or continuous sequence of movements of the various devices in any combination, if so desired in the medical procedure. An example of such a sequence in interventional medical procedures is a doddering motion comprising a rapidly alternating sequence of small advancements and retractions, which could be one method of finding a pathway through an occluded or partially occluded vessel in a patient, where the device could have a straight, curved, or actuated distal tip.

In one embodiment the motion control mechanism comprises an open device path bounded on opposite sides by a pair of wheels for drivingly engaging an elongate medical device in the device path. More specifically, the advancer can include a base having a slot with an open top and opposed sides therein, and a pair of opposed wheels on opposite sides of the slot. A drive mechanism is adapted to be connected to a motor, for turning at least one of the pair of opposed wheels. A cover can be movably mounted on the base for movement between a loading position in which the top of the slot is open to allow a portion of the at least one elongate device to be inserted into the slot between the wheels, and a drive position in which the cover at least partially blocks the top of the slot to retain the at least one elongate device therein. Each wheel can include a circumferential drive member that engages the at least one device in the slot in the drive position, the drive member configured to grip but not damage the device in contact therewith.

In some cases it may be convenient to also axially rotate the medical device(s), either with or without simultaneous advancement, for purposes of navigation and ease of access to particular anatomical regions and locations. The present invention is directed to also perform such types of axial rotation maneuvers in addition to advancement and retraction. It is worth noting that the control of device motion could be driven from a microprocessor or other controller that in turn interfaces to a computer with a Graphical User Interface or other types of user input such as joystick, mouse or customized user input device that directly or indirectly controls device motion. In some situations the computer could itself decide on the change of lower level control variables required to suitably move the device, based on high level instructions from a user that may be defined from any of a variety of user input mechanisms, and apply such control changes. Programmatic sequences of device movements could also be defined in this manner at a high level by the user, that would then be translated by the computer into a set of lower level control variable changes designed to accomplish the desired objectives.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 17 is a top perspective view of the configuration shown in FIG. 16;

FIG. 18 is a top perspective view of a sixth preferred embodiment of an advancer according to the principles of this invention for performing an over-the wire procedure;

FIG. 19 is a side elevation sectional view of a seventh preferred embodiment of an advancer in accordance with this invention configured to engage and turn a y-adapter fitting;

FIG. 20 is a side elevation sectional view of the advancer shown in FIG. 19;

FIG. 25 is a longitudinal cross sectional view of a rotatable catheter in accordance with the principles of this invention;

FIG. 26A is a partial transverse cross sectional view of the catheter in FIG. 25, illustrating a mechanism for the rotation of the rotatable portion;

FIG. 26B is a partial transverse cross sectional view of the catheter in FIG. 26A, after rotation of the rotatable portion;

FIG. 29 is a schematic diagram of a medical device motion system in accordance with the principles of this invention, shown with a telescoping medical device;

FIG. 30 is a schematic diagram of an alternate construction of the medical device motion system shown in FIG. 29, shown with a telescoping medical device.

Corresponding reference numerals indicate corresponding parts throughout the several views of the drawings.

DETAILED DESCRIPTION OF THE PREFERRED EMBODIMENTS

Figure 1:
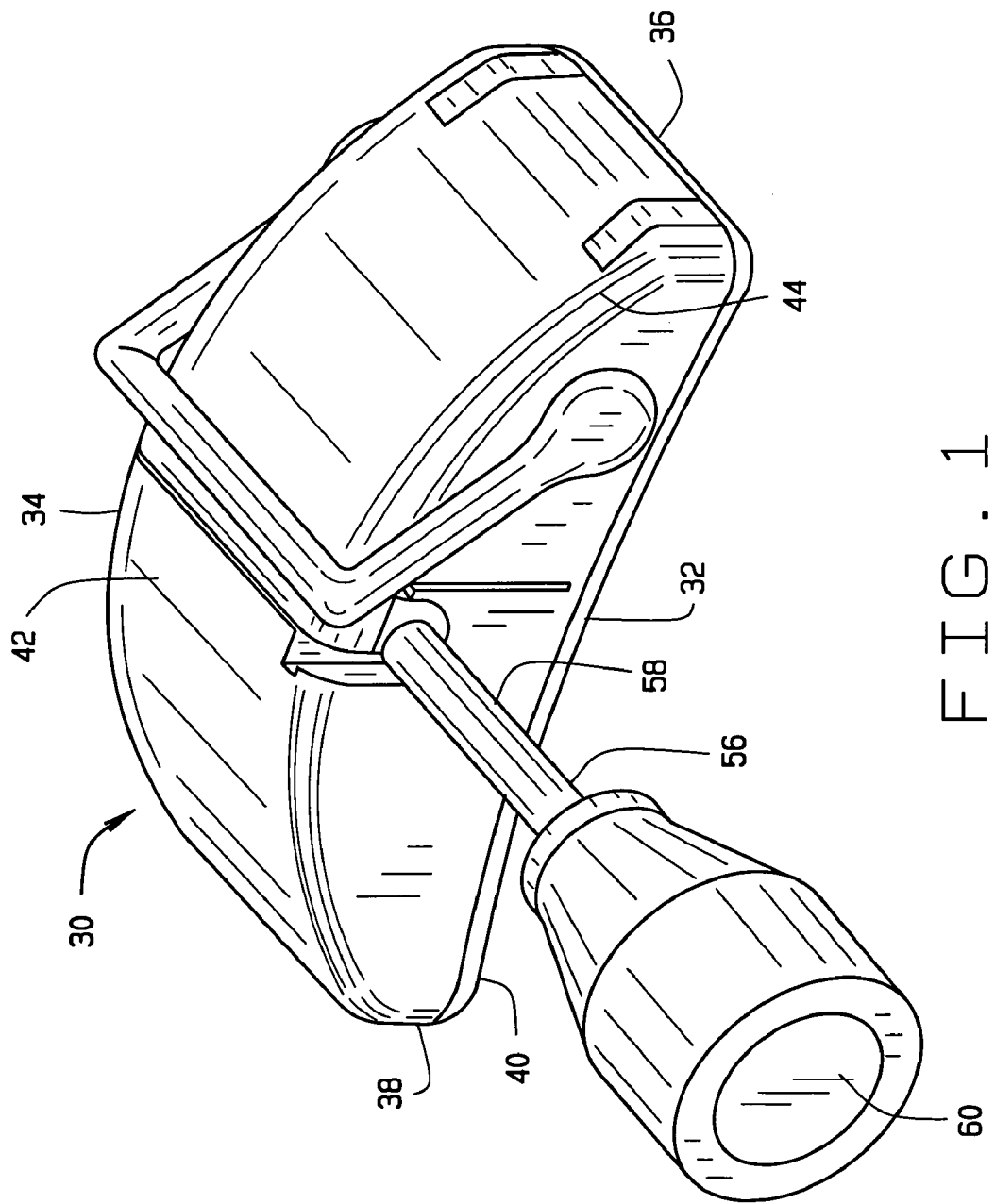
FIG. 1 is a front perspective view of a a first embodiment of a drive unit constructed according to the principles of this invention.
Figure 2:
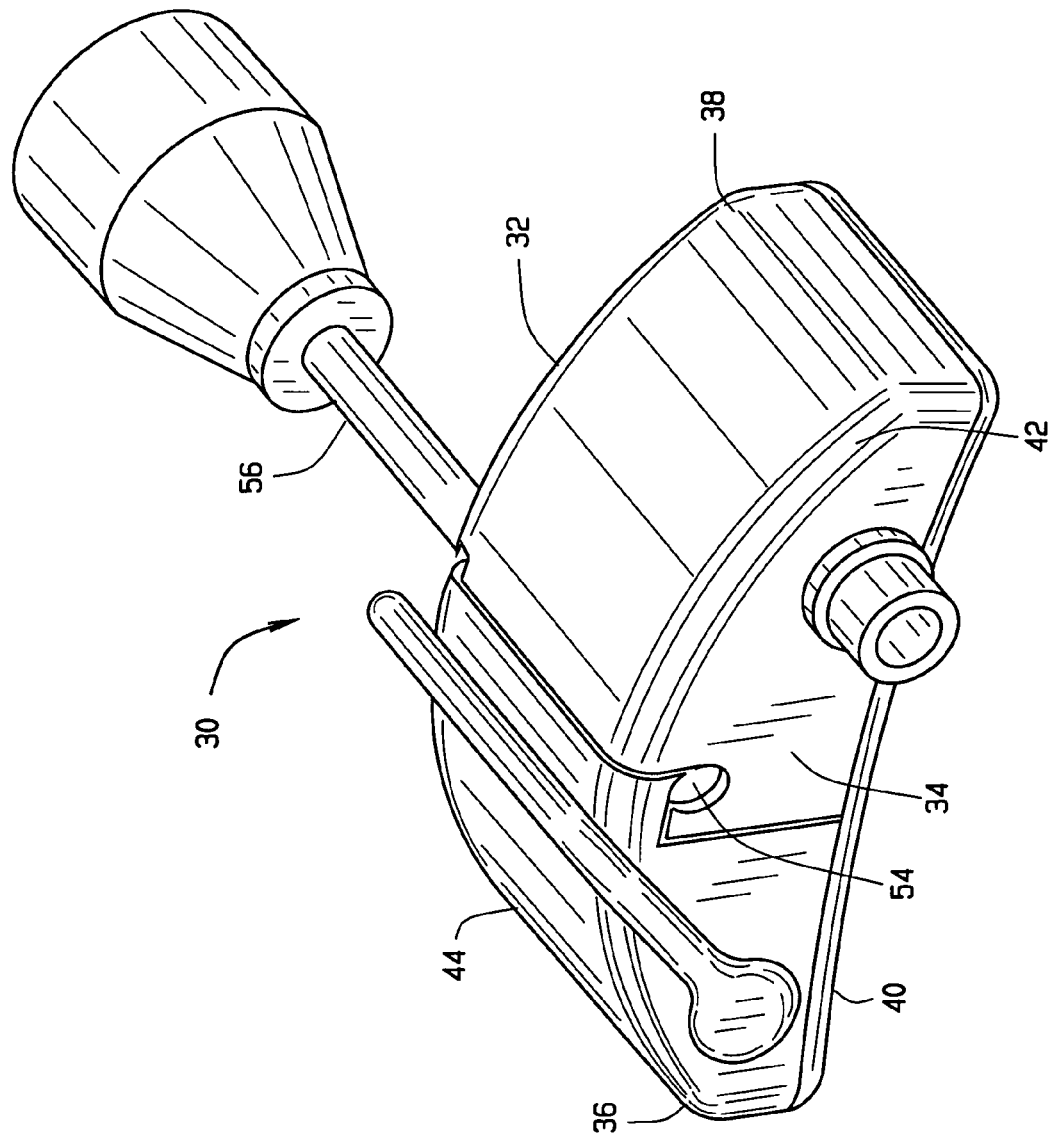
FIG. 2 is a rear perspective view of the drive unit shown in FIG. 1.
Figure 3:
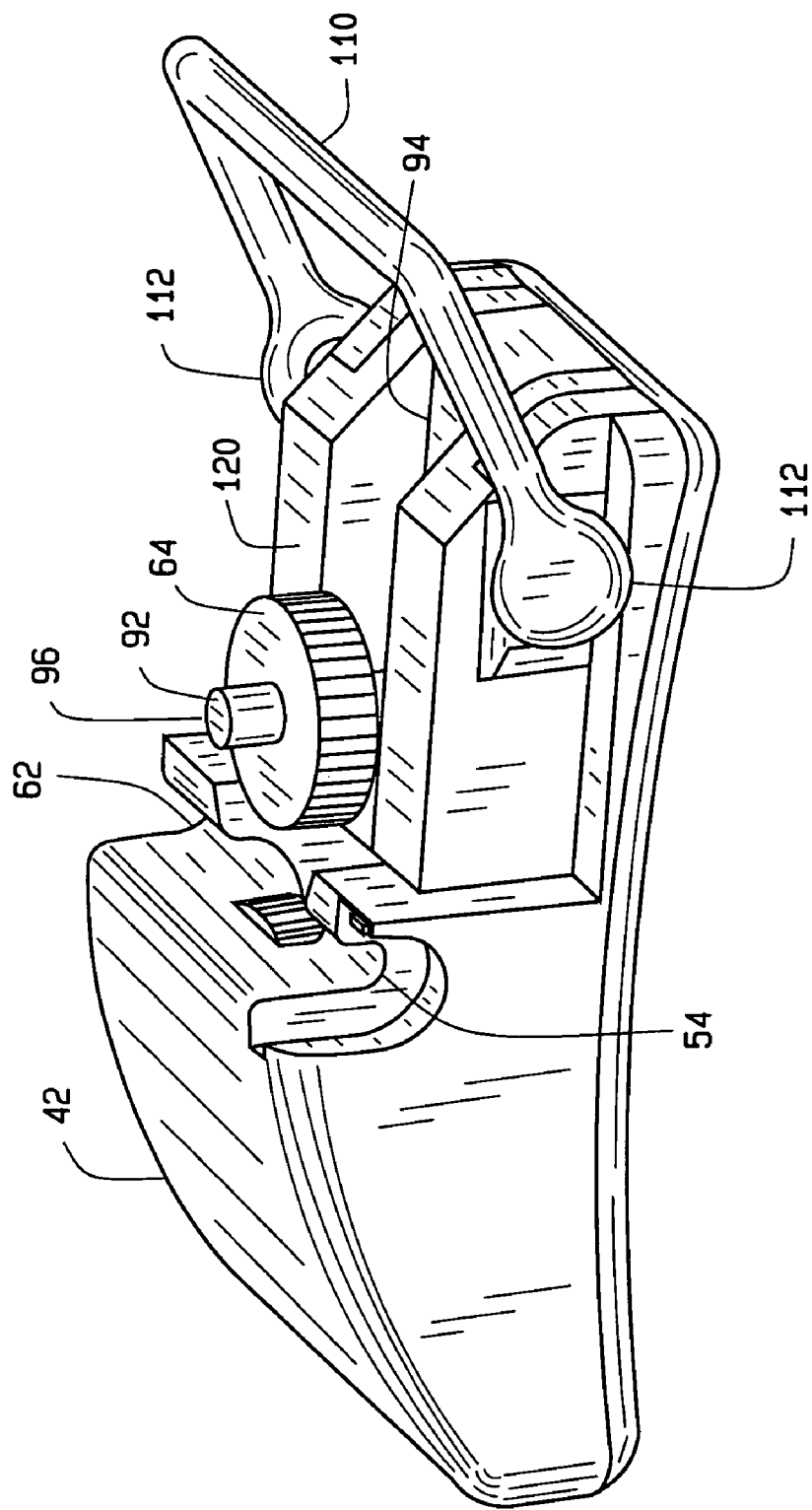
FIG. 3 is a front perspective view of the drive unit shown in FIG. 1, with the sliding cover removed.

The following description of the preferred embodiment(s) is merely exemplary in nature and is in no way intended to limit the invention, its application, or uses. Reference is made to U.S. patent application Ser. No. 10/138,710 filed on May 3, 2002, the disclosure of which is incorporated herein by reference in its entirety.

A first embodiment of a drive unit or advancer constructed according to the principles of this invention is indicated generally as 30 in FIGS. 1 through 7. The drive unit or advancer 30 is adapted for moving at least one elongate medical device such as a catheter and/or guide wire in the body of a subject. The advancer 30 is preferably small: for example in this first preferred embodiment it is about 2.6 inches long, about 1.1 inches wide (the longitudinal direction), and 1 inch high. The advancer 30 is preferably sterile, and is preferably sufficiently inexpensive to be disposable. The advancer 30 can be positioned close to the site where an elongate medical device, such as a guide wire or catheter is inserted or introduced into the subject's body (typically the femoral artery adjacent the patient's groin). The advancer 30 is preferably fabricated of non-magnetic materials, and more preferably substantially entirely of non-metallic materials. For example, the exterior of the advancer 30 can be made from a strong, durable plastic such as ABS, or other suitable material, and the interior components can be made from a strong, dimensionally stable plastic such as Delrin™ or other suitable material.

The advancer 30 is preferably substantially non-magnetic, i.e., it is sufficiently non-magnetic that it will not interfere with the operation of a magnetic surgery system that applies fields of 0.5 T or more to the operating region in a subject to orient the distal tip of the elongate medical device; that it will not interfere with the operation of a magnetic or other localization system for localizing the position and/or orientation of the distal end of the elongate medical device in the operating region; and that it will not interfere with magnetic or other imaging equipment, such as MR imaging equipment. (Of course, when the drive unit 30 is not used in connection with a magnetic navigation system or magnetic resonance imaging system, or magnetic localization system, or when it is used with non-magnetically actuated and steered devices, the magnetic properties of the drive unit are less important.

The advancer 30 has a front 32, a back 34, a left side 36 and a right side 38, and comprises a generally curved bottom 40. a base 42 fixedly mounted on the bottom, and a sliding cover 44 slidably mounted over the base on the bottom. The bottom 40 is curved for convenient mounting on the surface of the body of the subject—typically on the subject's upper thigh, adajacent the hip where there is convenient access to the femoral artery. However, the drive unit 30 can be mounted on, and used at, different locations. The base 42 is mounted on the bottom 40, for example with a pair of opposed pins (not shown) that extend through aligned holes 46 in the base and 48 in the bottom. The pins are preferably made of a non-magnetic, non-corrosive material such as stainless steel. The sliding cover 44 is movably attached to the bottom 40 by a pair of opposed pins (not shown) that extend through a pair of holes 50 in the cover (shown in FIG. 4) and a pair of horizontal slots 52 in the bottom 40 (shown in FIG. 5). Thus the cover 44 can be slid horizontally relative to the base 22 as limited by the slots 32, as further described below.

A slot 54 is formed in the base 42, extending from the front 32 to the back 34 for receiving a portion of an elongate medical device, such as a catheter or guide wire. A hemostasis valve adapter 56 is mounted at the front end 58 of the slot 54. A sheath or introducer can be connected to the hemostasis adapter 56, and the elongate medical device can extend through the slot 54 and into the sheath or introducer connected to the hemostasis adapter. The hemostasis adapter 56 preferably is flexible and has an interior surface 60 of Teflon® or other material having a coefficient of friction sufficiently low to permit the medical device to slide freely therein without buckling. The slot 54 in the base 40 is covered by the sliding cover 44, when the cover 44 is closed as further described below.

Figure 4:
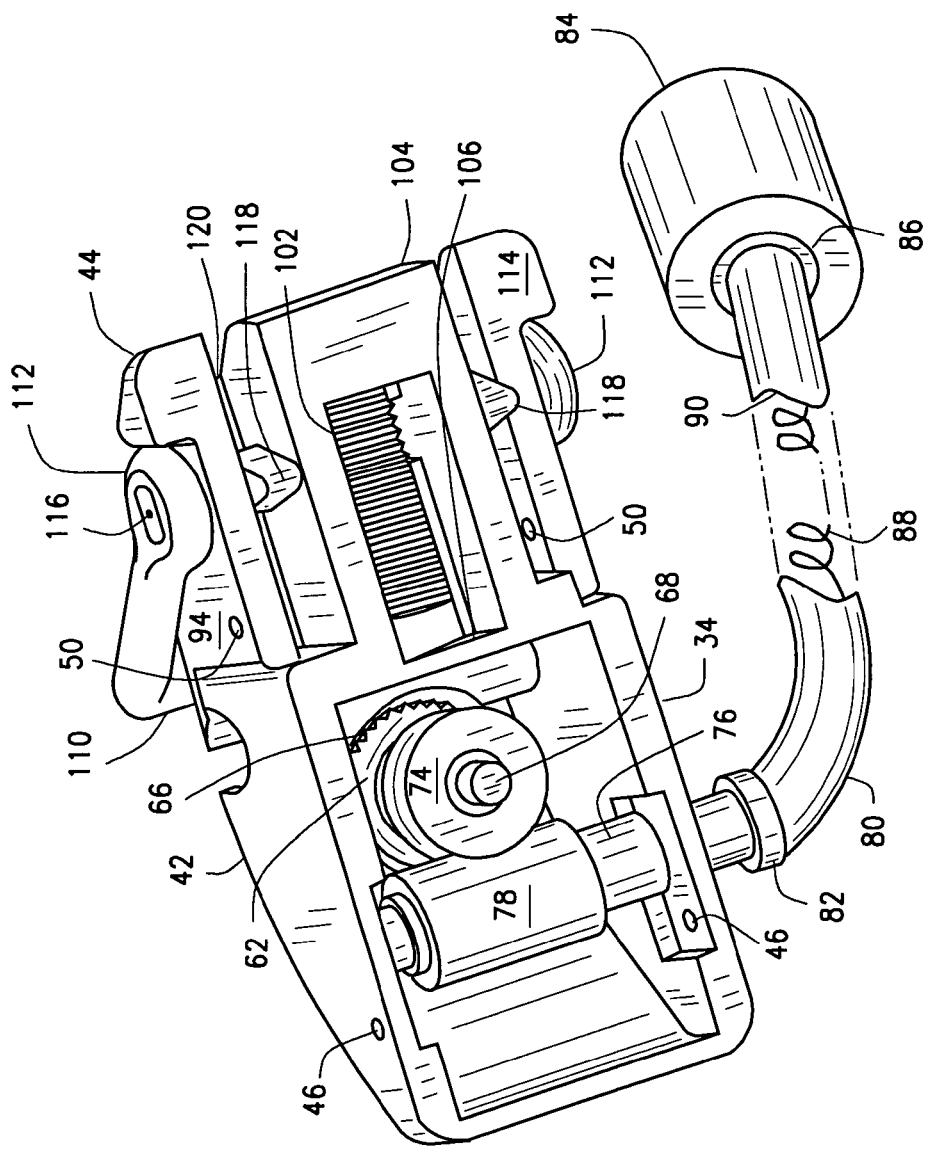
FIG. 4 is a bottom perspective view of the drive unit shown in FIG. 1, with the bottom removed.
Figure 5:
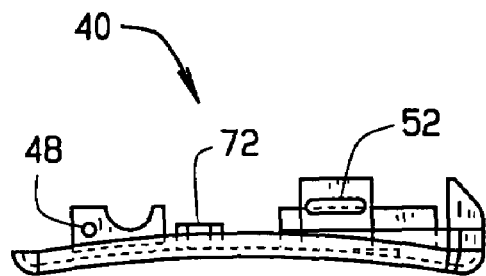
FIG. 5 is a side elevation sectional view of the bottom of the drive unit shown in FIG. 1.
Figure 6:
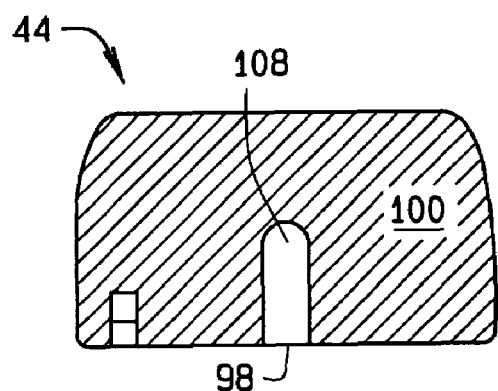
FIG. 6 is a plan sectional view of the inside of the sliding cover of the drive unit shown in FIG. 1.
Figure 7:
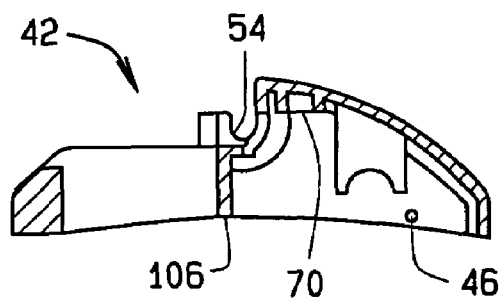
FIG. 7 is a side elevation sectional view of the base of the drive unit shown in FIG. 1.

Opposed wheels 62 and 64 protrude into the slot 54, preferably on opposite sides, to drivingly engage a medical device disposed therein. In this preferred embodiment, wheel 62 is a driven wheel, and wheel 64 is an idler wheel. Of course the wheel 64 could be the drive wheel and the wheel 62 the idler wheel, or both wheels could be drive wheels. The wheels 62 and 64 may be fabricated in various ways depending, for example, on the type, material and/or flexibility of the medical device to be driven through the drive unit 30. Thus the wheels 62 and 64 may be fabricated with small teeth 66 or serrations as shown in FIG. 4 (not to scale). The teeth 66 can grip a catheter as it is driven by the wheels. These small teeth may have a height of about 0.01 inch. Alternatively, the surfaces of wheels 62 and 64 can be fabricated of a soft material, for example, rubber, such that the wheels would conform to and engage slightly so as not to crush the medical device being driven by the wheels. In yet another embodiment, one or both of the wheels 62 and 64 can be circumferentially grooved for engaging an elongate medical device as further described below.

The driven wheel 62 is mounted on a shaft 68. The shaft 68 is rotatably mounted about an axis generally perpendicular to the bottom 40, between a socket 70 in the base 54 (shown in FIG. 7) and a socket 72 in the bottom 40 (shown in FIG. 5). A worm gear 74 is mounted on the shaft 68. A rigid drive shaft 76 is rotatably mounted longitudinally in the base 42 and extends through the back 34 of the advancer 30. The drive shaft 76 has a worm 78 that engages the worm gear 74 on the shaft 48.

A flexible drive shaft 80 is connected to the rigid drive shaft 56 via a connector 82, and to a drive motor 84 via a connector 86. The drive motor 84 is preferably a bi-directional controlled motor, for example, a stepper motor, that preferably can be controlled remotely In other embodiments, the motor 84 can be a servomotor. The flexible drive shaft 80 includes a ³⁄₁₆-inch-diameter flexible coil 88, preferably fabricated of non-magnetic stainless steel and covered by a flexible clear plastic tubing 90. The coil 88 is rotatable by the motor 84 in forward and reverse directions to provide bi-directional movement of the drive wheel 62. The flexible drive shaft 80 preferably is sterile for use within a sterile operating area. The drive shaft 80 also preferably is sufficiently long (for example, approximately four feet long) to allow it to be driven by the motor 84 while the motor remains outside the sterile surgical field. In other embodiments, the motor 84 is also sterile, is used within the sterile operating area, and is disposed of after completion of the operating procedure.

The idler wheel 64 is mounted on a shaft 92 that is snap-fitted into and extending vertically from a slot (not shown) in a floor 94 of the base 42. An upper end 96 of the shaft 92 fits in a groove 98 (shown in FIG. 6) extending transversely along an inner surface 100 of the sliding cover 44. A spring 102 is stretched, beneath the base floor 94, between an edge 104 of the sliding cover 44 and a vertical support 106 of the base 42. The spring 102 is preferably made of a non-magnetic, non-corrosive material such as stainless steel. The spring force of spring 102 thus pulls the sliding cover 44 horizontally toward the idler wheel shaft 92. When the cover 44 is in a closed position, the force of the spring 102 causes an end 108 of the groove 98 to press against the sham upper end 96. The idler wheel 64 thus is pressed against a medical device engaged between the idler wheel 64 and the driver wheel 62.

A generally U-shaped lever arm or handle 110 is used to open the sliding cover 44 Native to the base 42. Two legs 112 of the U-shaped handle are rotatably mounted over two sides 114 of the sliding cover 44 on a pair of opposed pivots 116 The pivots 116 extend toward each other through two cams 118. Although not attached to the base 42, each of the cams 118 is limited in its range of motion by an upper shelf 120 in the base 42. The cover 44 is biased by the spring 102 to a closed position against the shaft upper end 96, the cams are biased in an upright position as shown in FIG. 30, and the handle 110 is biased to lie flush against the cover 44.

To inset an elongate medical device into the drive unit 30, a user rotates the handle 110 away from the slot 54 in the base 42. As the handle 110 rotates on the pivots 116, the cams 118 also rotate to lie flat against the bottom 40. The pins extending through the holes 50 and bottom slots 52 move horizontally in the slots 52 away from the slot 54 in the base 42. The sliding cover 44 thus is opened sufficiently to uncover the slot 54 in the base 42. The groove 98 in the underside of the cover 44 allows the cover to be slid open, and subsequently closed, without disturbing the upper end 96 of the idle wheel shaft 92. The cams 118 are configured and positioned so as to lock the cover 44 in the open position.

At least one elongate medical device is loaded into the drive unit 30 by laying and pressing a length of the device into the slot 54 between the opposed wheels 62 and 64, until the device is engaged by the wheels, for example, between two grooves in wheels 62 and 64 as previously described. The user then pivots the handle 110 toward the slot 54, thereby causing the cams to return to the upright position. The sliding cover 44 is pulled by the spring 102 into a closed position over the elongate medical device. When the motor 84 is driven, the rigid drive shaft 76 turns, turning the worm 78, which in turn drives the worm gear 74, turning the drive wheel shaft 68 and thus the drive wheel 62. The medical device is advanced and/or retracted through the adapter 56 and attached sheath.

Figure 8:
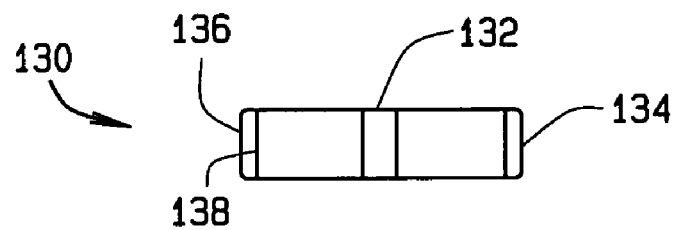
FIG. 8 is a side elevation sectional view of an embodiment of a wheel of a drive unit.
Figure 9:
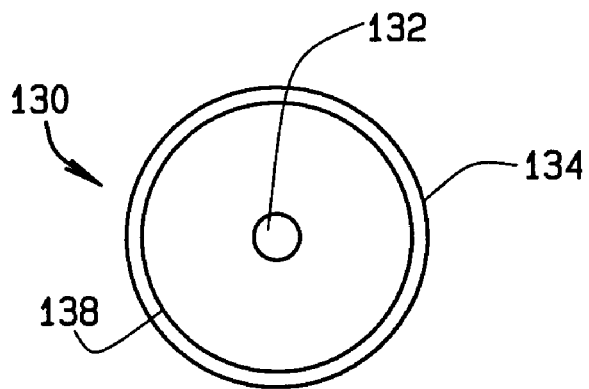
FIG. 9 is a plan sectional view of the wheel shown in FIG. 8.

Another embodiment of wheels 62 and 64 is indicated by reference number 130 in FIGS. 8 and 9. The wheel 130 has a central bore 132 configured to receive a shaft 68 or 92. A circumferential drive member 134 in the wheel 130 is configured to engage one or a plurality of elongate medical devices in the slot 54 (shown in FIG. 3) in position to be driven by the advancer 30. The drive member 134 is configured to grip but not damage an elongate device in contact therewith. In the embodiment shown in FIGS. 8 and 9, the drive member 134 includes a coating 136 on the surface 138 of the wheel 130. The coating 136 may be, for example, rubber, plastic (e.g., urethane) or silicone or other suitable material to resiliently engage a medical device.

Figure 10:
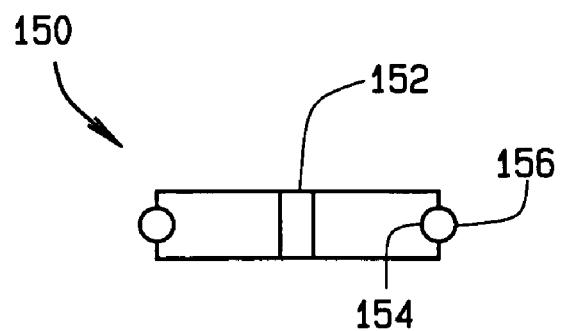
FIG. 10 is a side elevation sectional view of an alternate embodiment of a wheel of a drive unit.

A cross-sectional view of another embodiment of a wheel that can be used in the advancer 30 is indicated generally by reference number 150 in FIG. 10. The wheel 150 has a central bore 152 configured to receive a shaft 68 or 92. The wheel 150 also has a circumferential groove 154 therein, in which is positioned a circumferential drive member 156. The drive member 156 may be solid (and made for example, of rubber, plastic, or silicone), or hollow (and made, for example, of rubber, plastic or silicone tubing) to provide resilient engagement.

Advancer wheels and drive members may be configured in various ways to facilitate the driving of a plurality of elongate medical devices past the wheels. For example, the wheels and drive members may be configured to facilitate the selective advancement of one or both of two elongate devices, where one of the devices is at least partially disposed within the other device. For example the medical device could comprise an outer member and an inner member slidably received therein. The outer member may be moved while the inner member is held stable, for example, by holding or clamping a proximal end of the inner device. Additionally or alternatively, wheels and drive members may be configured to facilitate the movement of an inner member while an outer device is held stable, for example, by a hand or clamp at a proximal end of the outer member. Advancer wheels and drive members also may be configured to facilitate the movement of inner and outer devices together. Such combinations of devices may be advanced in the body in various ways, as further described below.

Referring again to FIGS. 1 through 7, one or both of the wheels 62 and 64 are interchangeable with other wheel(s), for example, during a medical procedure by an operating physician. A wheel 62 and/or 64 may be selected for use based on the type(s) and number of elongate devices to be advanced by the advancer 30. In such manner, a user can use the advancer 30 to advance, sequentially, more than one device during a procedure.

The spring 102 also may be interchangeable with another spring during a procedure. A spring may be selected for use based on the type(s) and number of elongate devices to be advanced by the advancer 30, and further based on the type(s) of wheels being driven and an amount of pressure desired to be exerted on the wheels by the spring.

Figure 11:
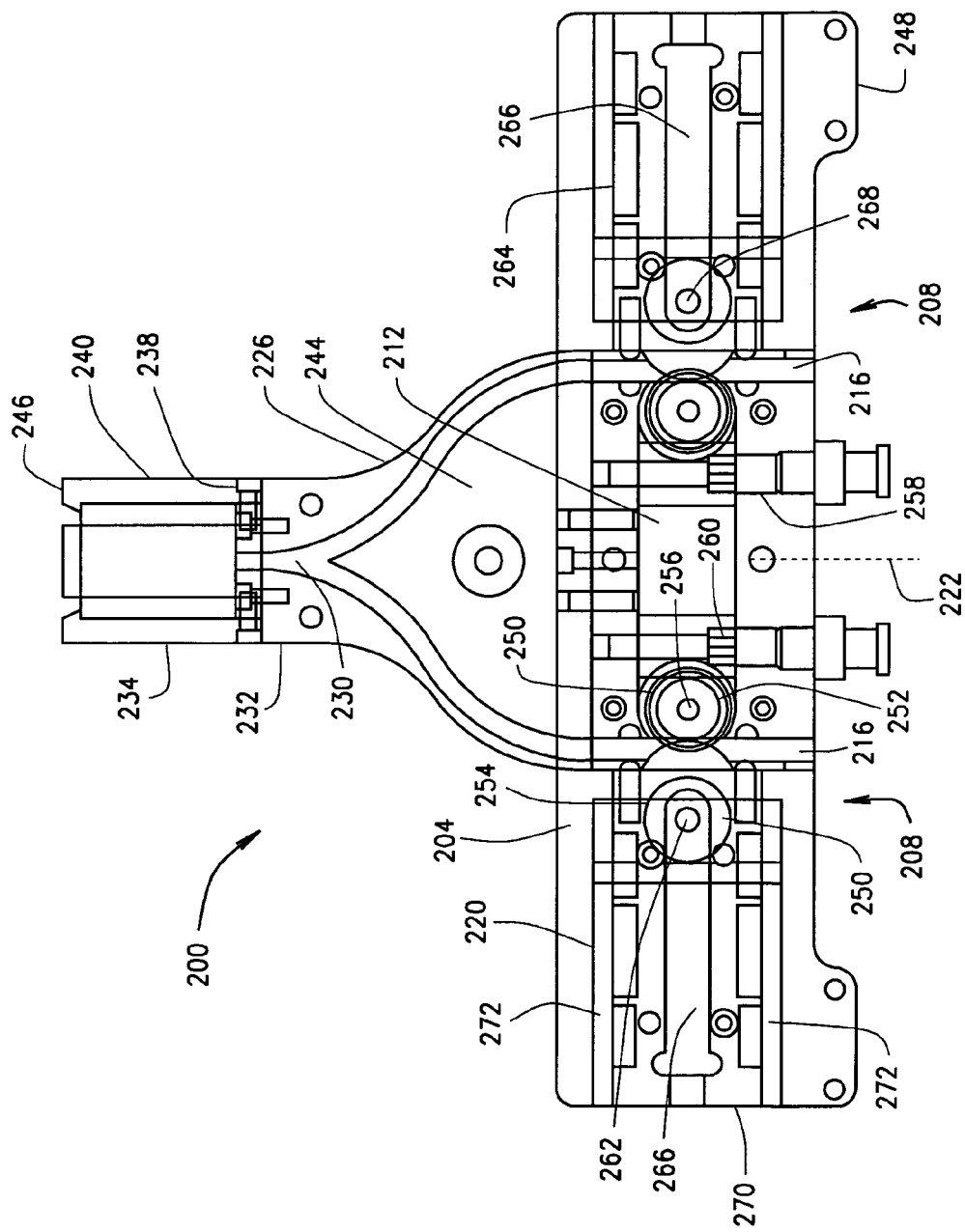
FIG. 11 is a plan sectional view of an a second preferred embodiment of an advancer according to the principles of this invention for advancing multiple devices.
Figure 12:
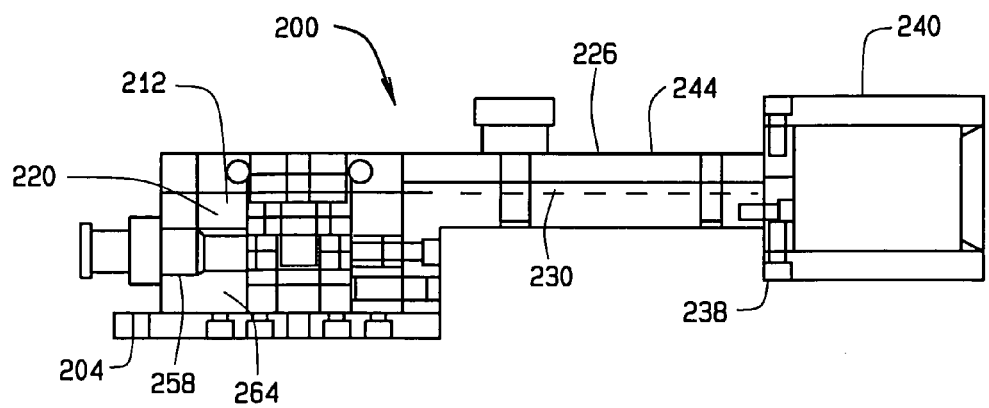
FIG. 12 is a side elevation sectional view of the advancer shown in FIG. 11.

A second preferred embodiment of an advancer in accordance with this invention is indicated generally by reference number 200 in FIGS. 11 and 12. The advancer 200 is adapted for advancing multiple devices. The advancer 200, like advancer 30, is preferably primarily non-magnetic and more preferably primarily non-metallic. Preferably, the advancer 200 is sufficiently non-magnetic and non-metallic that it can be left in place during MR imaging. The advancer 200 includes a base plate 204 supporting a plurality, e.g., a pair, of drive units indicated generally as 208. The drive units 208 have a common drive base 212. The base plate 204 preferably is about 6.5 inches wide (the transverse direction). The advancer 200 is configured to rest on or near a patient in the vicinity of an insertion site and can be mounted on a flexible arm as further described below.

The drive base 212 has a plurality, e.g., a pair, of longitudinal slots 216, each slot configured to hold at least one elongate medical device such as a catheter or guide wire. Each drive unit 208 also has a sliding cover 220, shown in an open position in FIG. 11. Each sliding cover 220 is movably attached to the base plate 204 by a pair of opposed pins (not shown) through a pair of holes (not shown) in the cover 220 and a pair of horizontal slots (not shown) in the drive base 212, such that the cover 220 can be slid horizontally away from and toward a longitudinal axis 222 of the drive base 212.

A guide base 226 extends distally from the drive base 212. The slots 216 extend into the guide base 226 and converge to form a common slot 230 at a distal end 232 of the guide base 226. A hemostasis clamp adapter 234 at the distal end 232 of the guide base includes a clamp base 238 and clamp arms 240. The guide base 226 has a cover 244. The advancer 200 is preferably about 4¾ inches long (between a distal end 246 of the hemostasis adapter 234 and a proximal end 248 of the base plate 204).

One or a plurality of elongate devices can be extended through the adapter 234 as further described below. The adapter 234 preferably is flexible and has an interior surface (not shown) of Teflon® or other material having a coefficient of friction sufficiently low to help resist buckling of an elongate device moving through the advancer 200. When closed, a cover 220 covers an associated slot 216 and retains an elongate device positioned and/or being driven in the covered slot 216. When closed, the guide base cover 244 covers the common slot 230 and retains an elongate device positioned and/or being driven in the common slot 230.

A corresponding pair of opposed wheels 250 protrude into each slot 216, which engage one or more medical devices in the slot 216. One of each pair of wheels 250 preferably is a driven wheel 252 and the other wheel of each pair is an idler wheel 254. The wheels 250 may be fabricated in various ways, as previously described with reference to the advancer 30, and may have drive members, also as previously described.

Each driven wheel 252 is mounted on a vertically mounted shaft. 256 in the advancer drive base 212. A worm gear (not shown) is mounted on each shaft 256. Each drive unit 208 has a rigid drive shaft 258 rotatably mounted longitudinally in the drive base 212 and extending proximally through the drive base 212. Each drive shaft 258 has a worm 260 that engages a corresponding one of the worm gears.

Two flexible drive shafts (not shown) are connected respectively to the rigid drive shafts 258 and to two drive motors (not shown). The drive motors are bi-directional controlled motors, for example, stepper motors, that preferably can be controlled remotely. In other embodiments, the motors can be servomotors. The flexible drive shafts and motors may be embodied as previously described in connection with the advancer 30 (shown in FIGS. 1 through 7).

Each idler wheel 254 is mounted on a shaft 262 snap-fitted into and extending vertically from a slot (not shown) in a floor or drive unit base 264. An upper end 268 of each shaft 262 fits in a groove (not shown) extending transversely along an inner surface of the corresponding sliding cover 220. Each of a pair of springs 266 is stretched, beneath the base floor 264, between an edge 270 of a corresponding sliding cover 220 and a vertical support (not shown) of the drive base 212. The springs 266 are of a non-magnetic, non-corrosive material such as stainless steel. A spring force thus pulls a sliding cover 220 horizontally toward the corresponding idler wheel shaft 262 (of course the spring could be arranged to provide a pushing force). When a cover 220 is in a closed position, the force of the corresponding spring 266 causes an end of the groove (not shown) to press against the shaft upper end 268. An idler wheel 254 thus is pressed against one or more medical devices engaged between the wheel 254 and the opposed driver wheel 252.

A generally U-shaped lever arm or handle (not shown) is used to open and close a sliding cover 220 relative to the drive base 212 as previously described with reference to the advancer 30 (shown in FIGS. 1-7). Two ends of each handle are rotatably mounted over two sides 272 of the corresponding sliding cover 220 on a pair of opposed pivots (not shown). The pivots further extend toward each other through two cams (not shown). Although not attached to the drive base 212, each of the cams is limited in its range of motion by an upper shelf (not shown) in the drive base 212. A cover 220 is biased by the corresponding spring 266 in a closed position against the corresponding shaft upper end 262, cams are biased in an upright position (not shown), and the corresponding handle is biased to lie flush against the cover 220.

To insert an elongate medical device into one of the drive units 208, a user rotates the appropriate handle (not shown) away from the corresponding slot 216. The corresponding sliding cover 220 thus is opened sufficiently to uncover the slot 216 in the drive base 212. The groove (not shown) in the underside of the cover 220 allows the cover to be slid open, and subsequently closed, without disturbing the upper end 268 of the idle wheel shaft 262 of the drive unit 208 being loaded. The corresponding cams (not shown) are positioned so as to lock the cover 220 in the open position.

At least one elongate medical device is loaded into the appropriate drive unit 208 by laying and pressing a length of the device into the slot 216 between the opposed wheels 252 and 254, until the device is engaged by the wheels, for example, between two grooves in wheels 252 and 254 as previously described with reference to FIGS. 8-10. The user then presses the appropriate handle toward the slot 216, thereby causing the appropriate cams to return to the upright position. The sliding cover 220 is pulled by the corresponding spring 266 into a closed position over the elongate medical device(s). When the corresponding drive unit motor (not shown) is driven, the corresponding rigid drive shaft 258 turns, turning the corresponding worm 260, which in turn drives the corresponding worm gear (not shown), turning the drive wheel shaft 256 and thus the corresponding drive wheel 252. The medical device is driven forward and/or backward in the corresponding slot 216 and the common slot 230, and through the adapter 234.

A second drive unit 208 may also be used to drive at least one elongate device. The user can load a device in the second drive unit 208, close the cover 220, and drive the device in the second slot 216. The user thus may use the two drive units 208 to drive a plurality of devices side by side, and/or with one device at least partly within another device, through the common slot 230 and through the adapter 234. The guide body cover 244 can be removed to facilitate the conjoining of two devices and preferably is replaced to cover the slots 216 and 230 after the devices are conjoined. Each of the devices can be driven independently of the other (subject to any frictional interaction between the devices) via the drive units 208.

Figure 13:
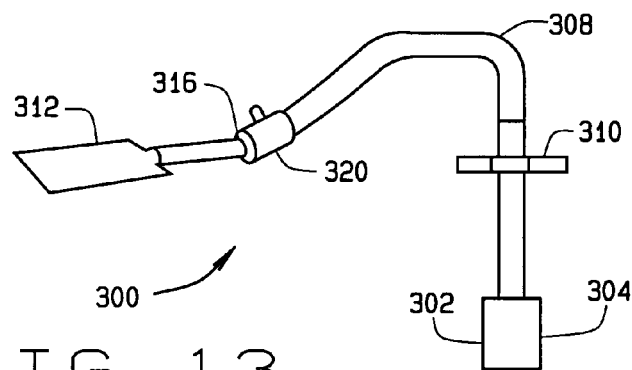
FIG. 13 is a front perspective view of an embodiment of a positioning arm useful with the various embodiments of advancers described herein.

A positioning arm for use with the various embodiments of advancers disclosed herein is indicated generally by reference number 300 in FIG. 13. A proximal end 302 of the arm 300 has an attachment device, e.g., a clamp 304, by which the arm 300 is anchorable, for example, to a ceiling or operating table. At least a portion 308 of the arm 300 can be made flexible for positioning the arm in a desired location. The arm 300 can be stiffened and locked in position using a lever 310. A shelf 312 extends from a ball joint 316 at a distal end 320 of the arm. An advancer or other device can be attached to the shelf 312. For example, the advancer base plate 204 (shown in FIGS. 11 and 12) can be screwed to the shelf 312. The advancer 200 thus can be positioned relative to a patient by moving the arm 300, swiveling the shelf 312 relative to the arm 300, and using the lever 310 to tighten the arm. The advancer 200 thus can be positioned above, but not necessarily in contact with, the patient.

The arm 300 may be fabricated at least primarily of non-magnetic stainless steel. In another embodiment, the arm 300 is fabricated at least primarily of plastic. Where fabricated of stainless steel, the arm 300 can be sterilizable and reusable. In one embodiment, the positionable portion 308 and lever 310 of the arm 300 are similar to that of known laparoscopic arms. In an embodiment in which the arm 300 is fabricated primarily of plastic, the arm can be "snap-locked" into a fixed position and may be disposable.

Figure 14:
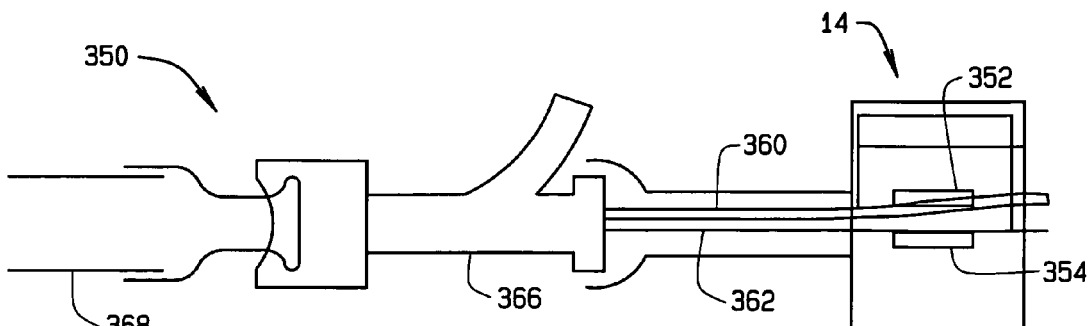
FIG. 14 is a side elevation sectional view of a third preferred embodiment of an advancer according to the principles of this invention for advancing multiple devices.

A third preferred embodiment of an advancer in accordance with this invention is indicated generally by reference number 350 in FIG. 14. The advancer 350 has an upper wheel pair 352 and a lower wheel pair 354. A catheter 360 is driven by the upper wheel pair 352. A guide wire 362 is driven by the lower wheel pair 354. The advancer 350 is configured with a y-connector 366 and a guide catheter 368, for example, for use in a rapid-wire exchange procedure as further described below.

Figure 15:
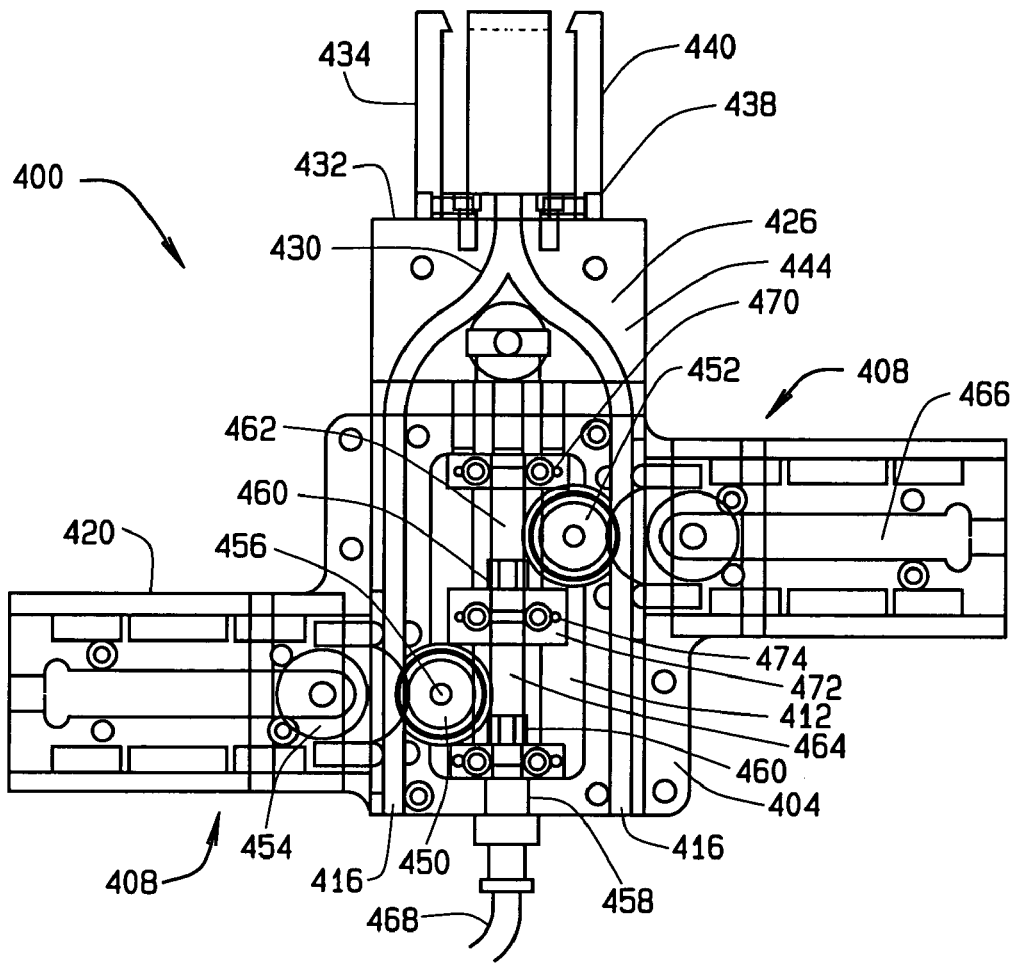
FIG. 15 is a plan sectional view of a fourth preferred embodiment of an advancer according to the principles of this invention for advancing multiple devices.

A fourth preferred embodiment of an advancer in accordance with this invention is indicated generally by reference number 400 in FIG. 15. The advancer 400 includes a base plate 404 supporting a plurality, e.g., a pair, of drive units 408 having a common drive base 412. The advancer 400 can be mounted a flexible arm as previously described in connection with the advancer 200.

The drive base 412 has a plurality, e.g., a pair, of longitudinal slots 416, each slot configured to hold at least one elongate medical device such as a catheter or guide wire. Each drive unit 408 also has a sliding cover 420, shown in an open position in FIG. 15. The sliding covers 420 are operable as described with reference to the sliding covers 220 (shown in FIGS. 11-12).

A guide base 426 extends distally from the drive base 412. The slots 416 extend into the guide base 426 and converge to form a common slot 430 at a distal end of the guide base 226. A hemostasis clamp adapter 434 at the distal end 432 of the guide base includes a clamp base 438 and clamp arms 440. The guide base 426 has a cover 444.

One or a plurality of elongate devices can be extended through the adapter 434, which is configured and operable as described with reference to FIGS. 11 and 12. When closed, a cover 420 covers an associated slot 416 and retains an elongate device positioned and/or being driven in the covered slot 416. When closed, the guide base cover 444 covers the common slot 430 and retains an elongate device positioned and/or being driven in the common slot 430.

Protruding into each slot 416 are a corresponding pair of opposed wheels 450, which engage one or more medical devices in the slot 416. One of each pair of wheels 450 preferably is a driven wheel 452 and the other wheel of each pair is an idler wheel 454. The wheels 450 may be fabricated in various ways, as previously described with reference to the advancer 10, and may have drive members, also as previously described.

Each driven wheel 452 is mounted on a vertically mounted shaft 456 in the advancer drive base 412. Worm gears (not shown) are mounted on each shaft 456. A drive shaft 458 is mounted longitudinally in the drive base 412. The drive shaft 458 includes coaxial distal and proximal sections 462 and 464, the distal section 462 extending through the proximal section 464. Each of the sections has a worm 460 that engages a corresponding one of the worm gears. The worm sections 462 and 464 are rotatably mounted in end sleeves 470 and a middle sleeve 472 attached to the drive base 412. Rotations of the sections 462 and 464 are facilitated by bearings 474 in the sleeves 470 and 472. The sections 462 and 464 are driven independently of each other via a flexible drive cable 468 having coaxial inner and outer drive shafts (not shown), and two drive motors (not shown) connected to the flexible drive cable 468. The drive motors are bi-directional controlled motors, for example, stepper motors, that preferably can be controlled remotely. In other embodiments, the motors can be servomotors.

Idler wheels 454 are mounted under the sliding covers 420 as described with reference to FIGS. 11 and 12. Each of a pair of springs 466 pulls a corresponding sliding cover 420 horizontally to press an idler wheel 454 against one or more medical devices engaged between the wheel 454 and the opposed driver wheel 452, also as described with reference to FIGS. 11 and 12.

A lever arm or handle (not shown) is used to open and close a sliding cover 420 relative to the drive base 412, and one or more elongate devices are inserted in the drive unit(s) 408, as previously described with reference to FIGS. 11 and 12. The user may use the two drive units 408 to drive a plurality of devices side by side, and/or with one device at least partly within another device, through the common slot 430 and through the adapter 434. The guide body cover 444 can be removed to facilitate the conjoining of two devices and preferably is replaced to cover the slots 416 and 430 after the devices are conjoined. Each of the devices can be driven independently of the other (subject to any frictional interaction between the devices) via the drive units 408.

As previously mentioned, the advancer 400 may include two stepper motors (not shown), for example, table-mount SilverMax™ NEMA 17 frame motors and gear boxes, available from Minarik Corporation of Glendale, Calif. The stepper motors are driven using the flexible drive shaft 468. One suitable dual drive shaft is available from Suhner Industrial Products Corporation of Rome, Ga.

The multiple-drive advancers 200, 350 and 400 allow top-loading, for example, of a catheter and a guide wire. One of the elongate devices can be driven while the other elongate device is held in place. Thus the advancers 200 and/or 400 can be used, for example, in a "rapid wire exchange" (RWE) procedure in conjunction with a magnetic surgery system such as that described in U.S. patent application Ser. No. 10/138,710 incorporated herein by reference. The magnetic system has, for example, a plurality of joysticks and/or a selectable joystick for physician interface with one or more medical devices as further described below.

Figure 16:
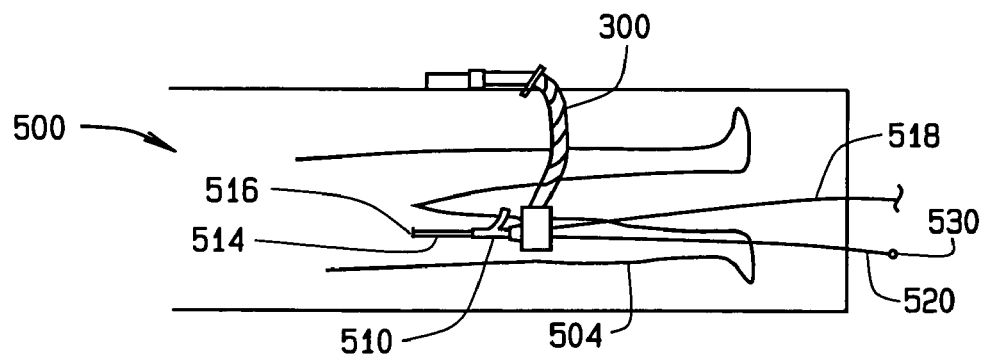
FIG. 16 is a top perspective view of a fifth preferred embodiment of an advancer according to the principles of this invention for performing a rapid-wire exchange procedure.
Figure 21:
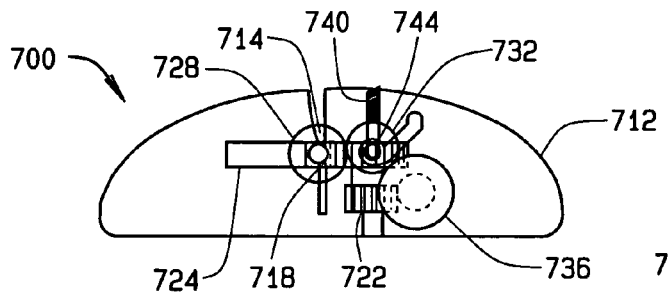
FIG. 21 is a front elevation sectional view of the advancer shown in FIG. 19.
Figure 22:
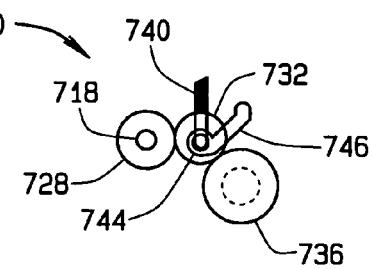
FIG. 22 is a front elevation sectional view of the advancer shown in FIG. 19.
Figure 23:
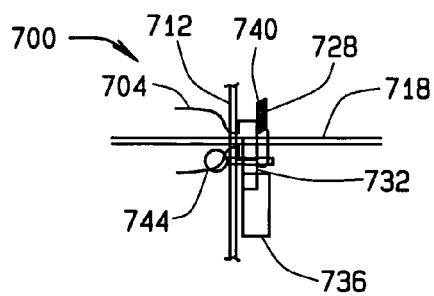
FIG. 23 is a side elevation sectional view of the advancer shown in FIG. 19.

A fifth preferred embodiment of the advancer in accordance with this invention for use in a RWE procedure, is indicated generally by reference number 500 in FIGS. 16 and 17. The advancer 500 is attached to a table-mounted flexible and lockable arm 300 (shown in FIG. 13) and positioned over a patient's leg 504. The leg 504 is restrained. A proximal end 508 of a guiding catheter 514 is connected to a hemostasis y-connector 510. A proximal end 526 of the y-connector 510 is connected to the hemostatic valve adapter 434 of the advancer 400.

A distal end (not shown) of the guide catheter 514 is guided, preferably manually, through an incision 516 into the ostium (not shown) of the patient. An injection and pressure measurement manifold, indicated by reference number 522, may be connected to a y-port 524 of the y-connector 510.

A guidewire 520 is back-loaded (inserted in the distal-to-proximal direction) into the distal end of a rapid-exchange catheter 518 with a guidewire lumen or "monorail" 532. The proximal end of the guidewire exits the monorail at a location proximal to the point of insertion into the monorail, albeit distal to the proximal end of the rapid-exchange catheter, while the distal end of the guidewire is positioned close to the distal end of the rapid-exchange catheter, either inside or outside the latter. The distal end of the rapid-exchange catheter (with the guidewire inside it) is then manually inserted into the guiding catheter 514 and the rapid-exchange catheter is manually advanced until the proximal portions of the rapid exchange catheter and the guidewire can be conveniently inserted into their respective drive units.

The wire 520 and catheter 518 then are next to each other between the guide catheter 514 and the advancer drive units 408. The guide wire is kept in its drive unit 408, and a proximal portion of the catheter 518 is inserted into the other drive unit 408. Thus the wire 520 and catheter 518 can be driven independently and remotely using the advancer 400.

The y-connector 510 may be, for example, a Co-Pilot® bleed-back control valve, part number 1003331, available from Guidant Corporation of Indianapolis, Ind. The guide catheter 514 can be, for example, a multi-purpose Guidant catheter in a size 6, 7 or 8F, available from Guidant Corporation of Indianapolis, Ind. A suitable rapid-wire exchange catheter 518 is, for example, a balloon micro-catheter, available from Boston Scientific Corporation, Natick, Mass. A suitable rapid-wire exchange guide wire 520 is, for example, a short-length guide wire.

Another advancer (not shown), for example, the advancer 30, may also be desirable for driving the guide catheter 514. In embodiments in which a guide catheter advancer is used, the guide catheter advancer would be positioned and possibly re-positioned during the procedure so as to maintain an appropriate range of motion relative to a proximal end of the guide catheter.

According to a sixth preferred embodiment of the present invention, two advancers, e.g., two advancers 30, are used as indicated generally in FIG. 18 by reference number 600, in an over-the-wire (OTW) procedure. Such a procedure may be, for example, a percutaneous transluminal coronary angioplasty and/or a stent delivery. A distal advancer 604 is used to advance a balloon catheter 606. A proximal advancer 608 is used for driving a guide wire 612. A guide catheter 616 is attached via a luer fitting 620 to a y-connector 624. The catheter advancer 604 is connected to a proximal end 626 of the y-connector 624. The balloon catheter 606 has an inflation lumen 628 through which the balloon can be inflated or a stent can be delivered.

The guide wire 612 is inserted into a guide wire lumen (not shown) of the balloon catheter 606. The guide wire 612 and balloon catheter 606 are driven together by the catheter advancer 604 through the guide catheter 616 into place within the patient. When it is desired to drive the guide wire 612 independently of the balloon catheter 606, the proximal end 634 of the balloon catheter 606 is held stable while the guide wire 612 is inserted into and driven by the wire advancer 608. The guide wire 612 thus can be driven backward relative to the catheter 606 during loading and advancement of the catheter 606.

A seventh preferred embodiment of an advancer in accordance with this invention is indicated generally by reference number 700 in FIGS. 19 through 23. The advancer 700 is configured to open and/or close a Touhy-Borst fitting 704 that connects a y-adapter 708 to the advancer 700. The advancer 700 has a body 712 with a slot 714. The advancer 700 is used to drive a catheter 718 through the slot 714 and the y-adapter 708. A drive gear assembly 722 that includes a drive shaft 720 and an idler wheel 724 is configured to drive the catheter 718. The catheter 718 extends through a y-adapter connector 728 that is connected to the Touhy-Borst fitting 704, fits in the slot 714 and is rotatable about the catheter 718.

A contact gear 732 that can contact the y-adapter connector 728 is configured to engage a rotator drive wheel 736. The gear 732 is normally not engaged with the wheel 736, which can rotate with the drive shaft 720. The wheel 736 rotates whenever the driveshaft 720 is active. When it is desired to tighten or loosen the Touhy-Borst fitting, a spring-loaded engagement switch 740 is activated, or alternatively an engagement lever 744 is manually activated, to cause the gear 732 to move, along an engagement guide 746, into engagement with the y-adapter connector 728. The engagement switch 740 can be activated using, for example, an electromechanical or hydraulic linear switch or activator 748. Thus the gear 732 can be engaged and disengaged by a remote user. The gear 732 is configured so as not to over-tighten the Touhy-Borst fitting.

The foregoing advancer 700 allows the Touhy-Borst fitting on the y-adapter to be opened and/or closed remotely. Thus the need for the fitting to be operated manually during a medical procedure, for example, during an interventional cardiology (IC) procedure, is reduced or eliminated.

Figure 24:
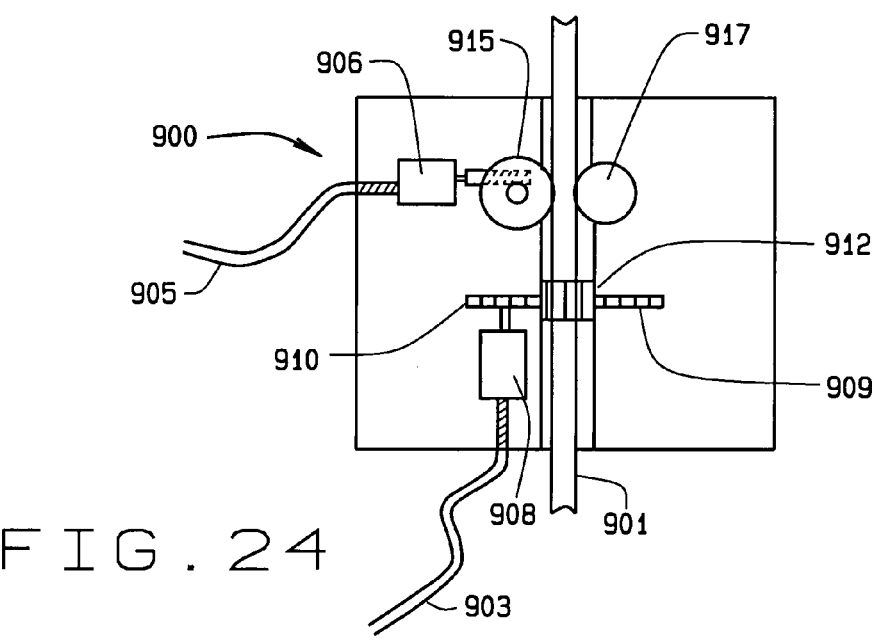
FIG. 24 is a top perspective view of an eight embodiment of this invention, where for simplicity a single device is shown being controlled.

Yet another embodiment is shown in FIG. 24. In this embodiment, the elongate medical device can be advanced by rotation of the distal pair of wheels 915 and 917, as well as rotated about its long axis by means of a geared sleeve that tightly engages the device for rotational purposes while at the same time permitting advancement and retraction of the device. For simplicity, this figure shows an advancer unit 900 engaging a single device 901. In addition to a drive cable 905, gear mechanisms 906 and advancement drive wheels 915 and 917, there is a second drive cable 903 that is connected to a gearbox unit 908, which in turn connects to a geared drive wheel 910. A geared sleeve 912 is sandwiched between the geared drive wheel 910 and a geared idle wheel 909. The medical device passes through the geared sleeve 912 and rotates with it as the flexible drive cable 903 rotates. This allows for transmission of the axial rotation to the distal end of the device, which could have a curved or bent shape, or a sharper angulation. This bent distal shape could itself be actuated by means of other actuation mechanisms such as cables passing within the device, small servo motors, external magnetic fields, electrostriction, hydraulic action, or a variety of other mechanisms known to those skilled in the art, so that the angular change in orientation over the distal portion is controllable. As the geared sleeve rotates, the shaped distal end also rotates and may be suitably directed within a patient's anatomy. For instance, if entry is desired into a particular vessel branch within the anatomy, the distal tip may be directed to assume a suitably convenient orientation in the manner described here. This orientation in some cases could then make the navigation of a second device such as a guidewire more convenient.

In one mode of operation, the drive cables can be driven so as to cause rapid alternating advancement and retraction movements of the medical device. Such a "doddering" mode can sometimes be useful for instance in finding a pathway through an occluded vessel, either with or without other conjunctive actuation of the distal tip of the device. In another operational mode, the gear arrangements can be configured to produce a mechanical vibration of the device, which can also be useful for some medical applications, for example to reduce or overcome friction.

It is possible to use a multiple device motion control mechanism as described herein to position and suitably orient the distal tip of an outer device, which then provides a pathway for an inner device to be passed within it and emerge from the distal end of the outer device to access or gain entry into a desired anatomical region within a patient. The converse arrangement, where an inner device is held fixed while an outer device is advanced over it to suitably access an anatomical region, can also be used in other situations. In some cases one of the devices can be manually advanced, while in others various combinations of manual and computerized motion control of the device can be employed. Likewise axial rotation of one or more of the devices could be manual or motor-driven.

It should be noted that the advancement and rotation of the medical device, doddering motions and extent of vibration could be controlled from a microprocessor or other control unit that can be interfaced to a control computer. The computer can have a variety of input modalities for a user to control the motion of operational mode of the medical device at a high level, such as a mouse, joystick or other forms of customized input device. The control unit can convert high-level user instructions into the control variables that actually define the desired device movements at a lower level. The computer can also drive other actuation modes such as magnetic field, cable lengths, servo motors, electrostrictive controls, hydraulic or other modes known to those skilled in the art that control the distal tip of the device so that the device can be suitably navigated to desired parts of the anatomy. Sequences of moves of different types can also be applied to the device under computer control.

The description of the invention is merely exemplary in nature and, thus, variations that do not depart from the gist of the invention are intended to be within the scope of the invention. Such variations are not to be regarded as a departure from the spirit and scope of the invention.

An embodiment of a rotatable catheter adapted for use with the various embodiments of motion control systems of the present invention is indicated generally as 1000 in FIG. 25. As shown in FIG. 25, the catheter 1000 comprises a proximal portion 1002 and a distal portion 1004. The proximal portion 1002 is preferably elongate and flexible. The distal portion 1004 can be generally straight, as shown, or it can has a preformed shape, such as a bend or a curve, so that rotation of the distal portion 1004, as described below, changes the position and orientation of the distal end of the catheter 1000. The distal end of the proximal portion 1002 and the proximal end of the distal portion 1004 are configured to interfit so that the distal end portion 1004 can rotate freely with respect to the proximal end portion, but is securely retained thereon. Of course, the distal portion 1004 could be mounted on the proximal portion in some other way, provided that the distal portion 1004 is freely rotatable yet securely retained on the proximal portion 1002.

A control element 1006 extends from the distal portion 1004, through a lumen 1008 in the proximal portion 1002. The control element 1006 is preferably flexible, but torsionally stable, so that rotation of the control element 1006 rotates the distal portion 1004. The control element 1006 may be sufficiently long to extend from the proximal end of the proximal portion 1004, where it can be conveniently rotated to cause the distal portion 1004 to rotate. Alternatively, the control element 1006 may be shaped with corners or a flat sides so that the control element 1005 can be engaged and turned through the wall 1010 of the proximal portion 1002. For example, the control element 1006 can be engaged by rollers 1012 and 1014 that compress the wall 1010 of the proximal portion 1002. As illustrated in FIGS. 26A and 26B, as the rollers 1012 and 1014 revolve around the longitudinal axis of the catheter 1000, the rollers can rotate around their respective axes, rolling over the surface of the wall 1010 while urging the control element 1006 to rotate within the lumen 1008. Alternatively, the rollers 1012 and 1014 can slide over the surface of the wall 1010, as they revolve around the proximal portion 1002 and rotate the control element 1006.

Figures 27, 28:
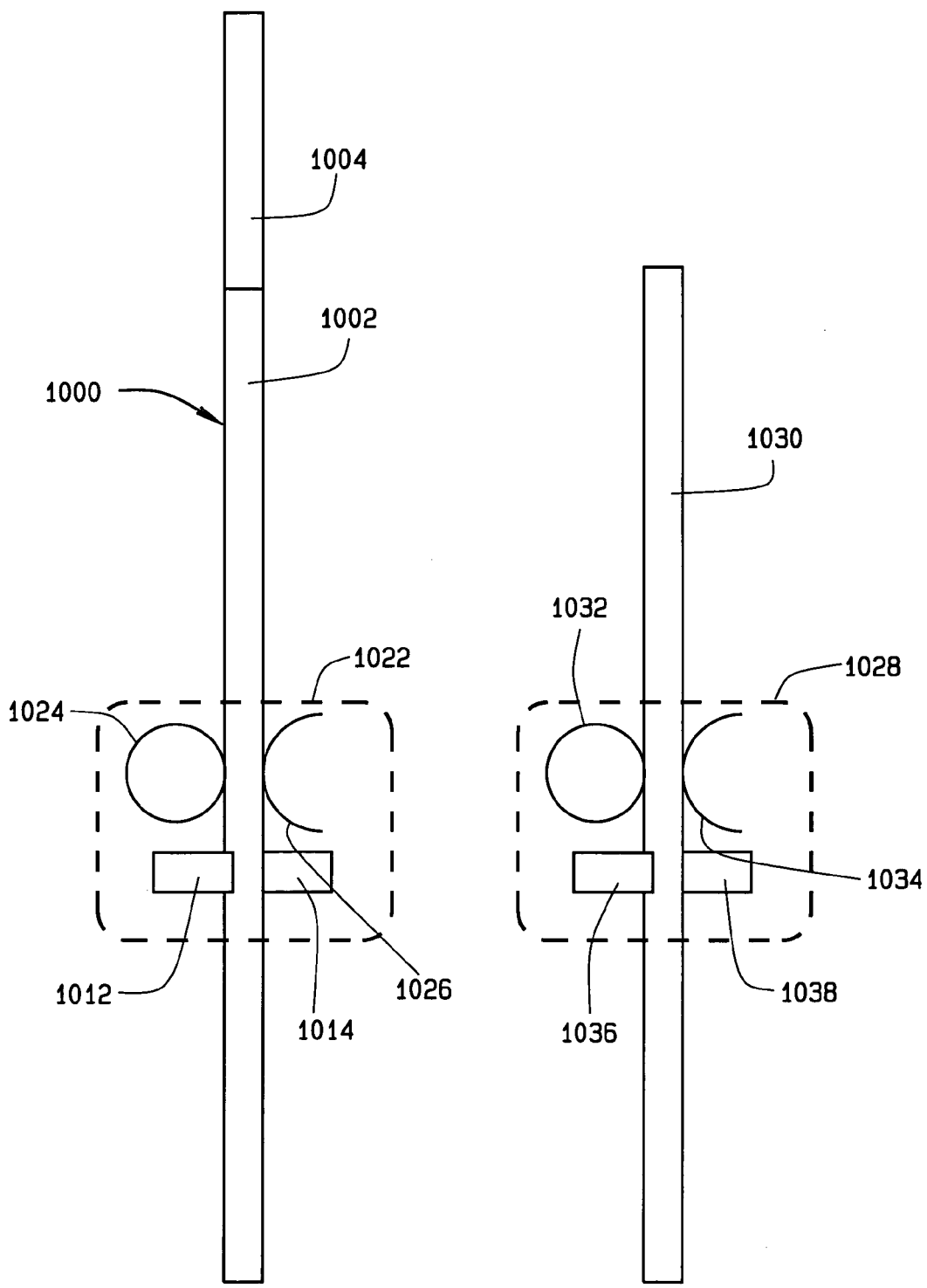
FIG. 27 is a schematic diagram of a medial device motion system, in accordance with the principles of this invention shown with a medical device with a rotatable portion.
FIG. 28 is a schematic diagram of a medical device motion system in accordance with the principles of this invention.

The rotatable catheter 1000 can form part of a medical device and medical device motion system combination as shown schematically as 1020 in FIG. 27. The combination 1020 comprises an elongate medical device, such as rotatable catheter 1000, and a medical device motion system 1022. The medical device motion system 1022 comprises at least one drive element, such as drive wheel 1024. In some embodiments, the medical device motion system 1022 further comprises a second wheel, which can be a drive wheel or a driven wheel, and in other embodiments the medical device motion system further comprises a smooth support 1026, along which the catheter 1000 can freely slide. The medical device motion system 1022 also comprises rollers, such as 1012 and 1014, which can revolve around the axis of the catheter 1000, to a rotate control element 1006 extending through lumen 1008 in the proximal portion 1002, and thus rotate the distal portion 1004.

An alternative embodiment of the medical device motion system 1022 is indicated generally as 1028 in FIG. 28. The medical device motion system 1028 can be used to advance an elongate medical device, such as a conventional catheter 1030. The medical device motion system 1028 comprises at least one drive element, such as drive wheel 1032. In some embodiments, the medical device motion system 1028 further comprises a second wheel, which can be a drive wheel or a driven wheel, and in other embodiments the medical device motion system further comprises a smooth support 1034, along which the catheter 1030 can freely slide. The medical device motion system 1028 also comprises at least one rotational drive element, such as a drive wheel 1036, which engages and rotates the catheter 1030 about its longitudinal axis. The medical device motion system 1028 can also include a second wheel 1038, which can engage the catheter 1030. The second wheel 1038 can be a driven wheel, or an idler wheel. Thus the system 1028 can used to advance and retract a device, such as catheter 103, and to rotate a device such as catheter 1030, either clockwise or counterclockwise.

Another embodiment of a medical device and medical device motion system combination is shown schematically as 1050 in FIG. 29. The combination 1050 comprises a telescoping catheter 1052, and first and second medical device motion systems 1054 and 1056. The telescoping catheter 1052 comprises an outer sheath member 1058, having a proximal end 1060, a distal end 1062, and a lumen therebetween. The telescoping catheter further comprises an inner member 1064, having a proximal end 1066, and a distal end 1068, slidably received in the lumen of the outer sheath 1058, and telescopable from the distal end 1062 of the outer sheath 1058. The section of the inner member 1064 adjacent the distal end 1068 can have a preformed configuration such as a bent or curved configuration (shown in FIG. 30), or the distal end could have a straight or shapeless configuration (shown in FIG. 29). The combination 1050 preferably also includes a first medical device motion system 1054 comprising at least one drive element, such as drive wheel 1070. In some embodiments, the medical device motion system 1050 further comprises a second wheel, which can be a drive wheel or a driven wheel, and in other embodiments the medical device motion system further comprises a smooth support 1072, along which the outer sheath 1058 can freely slide. The medical device motion system 1054 also comprises rollers, such as 1074 and 1076, which can revolve around the axis of the catheter 1052, to rotate inner member 1064 in the outer member 1058. The combination 1050 further includes a second medical device motion system 1056, which comprises at least one drive element, such as drive wheel 1078. In some embodiments, the second medical device motion system 1050 further comprises a second wheel, which can be a drive wheel or a driven wheel, and in other embodiments the medical device motion system further comprises a smooth support 1080, along which the inner element 1064 can freely slide.

The driver in system 1054 (wheel 1070 in the preferred embodiment) preferably engages the outer sheath 1058 sufficiently to cause the outer sheath 1058 to frictionally engage the inner member 1064, so that the driver can drive both the outer sheath 1058 and the inner member 1064. The driver in system 1056 (wheel 1078 in the preferred embodiment) preferably engages the inner member 1064 sufficiently to overcome the friction between the inner member 1064 and the outer sheath 1058, to drive the inner member 1064 independently of outer sheath 1058. When it is desired to drive the inner member 1064 and the outer sheath 1058 together, both the systems 1054 and 1056 can be used together, or the system 1056 can be disengaged so that it does not impair the movement of the inner member 1064. When it is desired to drive the inner member 1064 alone, the system 1056 can be operated alone, and the system 1054 helps retain the outer sheath 1058 in its position.

Another embodiment of a medical device and medical device motion system combination is shown schematically as 1090 in FIG. 30. The combination 1090 comprises a telescoping catheter 1092, and first and second medical device motion systems 1094 and 1096, respectively. The telescoping catheter 1092 comprises an outer sheath member 1098, having a proximal end 1100, a distal end 1102, and a lumen therebetween. The telescoping catheter 1092 further comprises an inner member 1104, having a proximal end 1106, and a distal end 1108, slidably received in the lumen of the outer sheath 1098, and telescopable from the distal end 1102 of the outer sheath 1098. The section of the inner member 1104 adjacent the distal end 1108 can have a preformed configuration such as a bent or curved configuration (shown in FIG. 30), or the distal end could have a straight or shapeless configuration (shown in FIG. 29). The first medical device motion system 1094 comprises at least one drive element, such as drive wheel 1110. In some embodiments, the medical device motion system 1094 further comprises a second wheel, which can be a drive wheel or a driven wheel, and in other embodiments the medical device motion system further comprises a smooth support 1112, along which the outer sheath member 1098 can freely slide. The combination 1090 further includes a second medical device motion system 1096, which comprises at least one drive element, such as drive wheel 1114. In some embodiments, the second medical device motion system 1096 further comprises a second wheel, which can be a drive wheel or a driven wheel, and in other embodiments the medical device motion system further comprises a smooth support 1116, along which the inner element 1104 can freely slide. The medical device motion system 1096 also comprises at least one drive roller, and in this preferred embodiment a pair of opposed rollers 1118 and 1120 to rotate the inner member 1104 in the outer member 1098.

What is claimed is:

1. An advancer for moving at least one elongate medical device, the advancer comprising:

a base having a slot with an open tope and opposed sides therein;

a pair of opposed wheels having positions on opposite sides of the slots;

a drive mechanism adapted to be connected to a motor, for turning at least one of the pair of opposed wheels to provide at least one drive wheel; and a cover movably mounted on the base for movement relative to the slot and the pair of opposed wheels, such that the position of the pair of opposed wheels remains fixed while the cover moves away from the slot and pair of opposed wheels, the cover being movable between a loading position in which the top of the slot is open to allow a portion of the at least one elongate device to be inserted into the slot between the wheels, and a drive position in which the cover at least partially blocks the top of the slot to retain the at least one elongate device therein.

2. The advancer of claim 1 wherein at least one of the drive wheels comprises a plurality of serrations.

3. The advancer of claim 1 wherein at least one of the drive wheels comprises a coating on the wheel.

4. The advancer of claim 1 wherein at least one of the drive wheels comprises tubing extending around the wheel.

5. The advancer of claim 1 wherein at least one of the drive wheels comprises at least one of rubber, plastic and urethane.

6. The advancer of claim 1 wherein upon movement of the cover to a position away from the slot and pair of wheels, at least one of the drive wheels is removable and replaceable by another drive wheel during a medical procedure.

7. The advancer of claim 1 wherein upon movement of the cover to a position away from the slot and pair of wheels, at least one of the wheels is removable and replaceable by another wheel during a medical procedure.

8. The advancer of claim 1 wherein a plurality of elongate medical devices are inserted into the slot, the drive wheels configured to allow a first of the devices to be driven while allowing a second of the devices not to be driven.

9. The advancer of claim 8 wherein the first device is at least partially inside the second device.

10. The advancer of claim 8 wherein the second device is held at a proximal end of the second device while the first device is being driven.

11. The advancer of claim 8 wherein each of the first and second devices is selectively driven by a user remote from the advancer.

12. The advancer of claim 1 further comprising a spring that, when the cover is in the drive position, pulls one of the wheels against the at least one elongate device in the slot and toward the other wheel so as to provide a pressure by the wheels against the device; and wherein the spring is replaceable by another spring during a medical procedure.

13. The advancer of claim 1 further comprising a filling for a hemostasis valve adapter, the drive mechanism further comprising:

a drive shaft for driving at least one wheel of the wheel pair;
an adapter engagement wheel mounted the drive shaft; and
an adapter engagement gear configured to engage and turn a valve adapter in the filling when turned by the adapter engagement wheel.

14. An advancer for moving at least one elongate medical device, the advancer comprising:

a base having a slot with an open top and opposed sides therein;
a pair of opposed wheels having positions on opposite sides of the slots;
a drive shaft operable by a motor to drive at least one of the pair of opposed wheels to provide at least one drive wheel;
a slot cover that is movable relative to the slot and the pair of opposed wheels, such that the position of the pair of opposed wheels remains fixed while the cover moves away from the slot and pair of opposed wheels, the cover being movable between a loading position in which the top of the slot is open to allow a portion of the at least one elongate device to be inserted into the slot between the wheels, and a drive position in which the cover at least partially covers the top of the slot;
a hemostasis valve adapter filling at an end of the slot;
an adapter engagement wheel mounted on the drive shaft; and
an adapter engagement gear configured to engage and turn a valve adapter in the fitting when turned by the adapter engagement wheel.

15. The advancer of claim 14 further comprising an engagement device configured to cause the adapter engagement wheel to alternately engage and disengage the adapter engagement gear relative to the fitting.

16. The advancer of claim 15 wherein the engagement device comprises a remotely operable switch.

* * * * *

UNITED STATES PATENT AND TRADEMARK OFFICE
CERTIFICATE OF CORRECTION

PATENT NO. : 7,635,342 B2
APPLICATION NO. : 10/858485
DATED : December 22, 2009
INVENTOR(S) : Ferry et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1478 days.

Signed and Sealed this

Ninth Day of November, 2010

David J. Kappos
*Director of the United States Patent and Trademark Office*